(12) United States Patent
Jeon et al.

(10) Patent No.: US 9,739,691 B2
(45) Date of Patent: Aug. 22, 2017

(54) SLIDE ASSEMBLY

(71) Applicant: CYTOGEN CO., LTD., Seongnam-si, Gyeonggi-do (KR)

(72) Inventors: Byung Hee Jeon, Seongnam-si (KR); Jong Kil Lee, Incheon (KR)

(73) Assignee: Cytogen Co., Ltd., Seongnam-si, Gyeonggi-do (KR)

( * ) Notice: Subject to any disclaimer, the term of this patent is extended or adjusted under 35 U.S.C. 154(b) by 0 days.

(21) Appl. No.: 14/905,273

(22) PCT Filed: Jul. 15, 2014

(86) PCT No.: PCT/KR2014/006306
§ 371 (c)(1),
(2) Date: Jan. 14, 2016

(87) PCT Pub. No.: WO2015/008991
PCT Pub. Date: Jan. 22, 2015

(65) Prior Publication Data
US 2016/0299042 A1    Oct. 13, 2016

(30) Foreign Application Priority Data

Jul. 15, 2013   (KR) .................. 10-2013-0083175
Jul. 15, 2013   (KR) .................. 10-2013-0083176

(51) Int. Cl.
*G01N 1/31*    (2006.01)
*G02B 21/34*   (2006.01)
(Continued)

(52) U.S. Cl.
CPC .......... *G01N 1/312* (2013.01); *B01L 3/50273* (2013.01); *B01L 3/502715* (2013.01);
(Continued)

(58) Field of Classification Search
CPC  G01N 1/312; B01L 3/502715; B01L 3/50273
See application file for complete search history.

(56) References Cited

U.S. PATENT DOCUMENTS 4,477,575 A  * 10/1984  Vogel ................ B01D 39/2017
                                                    210/509
4,863,591 A     9/1989  Dionne
(Continued)

FOREIGN PATENT DOCUMENTS

JP        2-1551 A    1/1990
JP        9-61723 A   3/1997
(Continued)

OTHER PUBLICATIONS

International Search Report dated Oct. 14, 2014 of PCT/KR2014/006306 which is the parent application and its English translation—5 pages.

(Continued)

*Primary Examiner* — Jill Warden
*Assistant Examiner* — Jyoti Nagpaul
(74) *Attorney, Agent, or Firm* — Knobbe Martens Olson & Bear LLP

(57) ABSTRACT

Disclosed is a slide assembly for a cytospin. The slide assembly includes: a slide having a hole formed in a predetermined position and including a mesh filter installed on a lower surface of the slide in alignment with the hole, the mesh filter having a plurality of filtering holes; and a filter card disposed below the slide so as to make contact with the lower surface of the slide. The slide assembly has an effect of preventing a loss of cells to be inspected and an effect of enabling accurate qualitative and quantitative analysis of inspection targets.

5 Claims, 5 Drawing Sheets

(51) Int. Cl.
  *B01L 3/00* (2006.01)
  *G01N 1/28* (2006.01)
  *G01N 1/40* (2006.01)

(52) U.S. Cl.
  CPC ......... *G01N 1/2813* (2013.01); *G01N 1/4077* (2013.01); *G02B 21/34* (2013.01); *B01L 2200/027* (2013.01); *B01L 2300/069* (2013.01); *B01L 2300/0681* (2013.01); *B01L 2300/0822* (2013.01); *B01L 2300/0887* (2013.01); *B01L 2400/0406* (2013.01); *G01N 2001/4088* (2013.01)

(56) References Cited

U.S. PATENT DOCUMENTS

| | | |
|---|---|---|
| 6,001,151 A | 12/1999 | Elshout |
| 6,750,039 B1 | 6/2004 | Bargoot et al. |
| 2005/0239216 A1 | 10/2005 | Feistel |
| 2009/0120865 A1 | 5/2009 | Chung et al. |

FOREIGN PATENT DOCUMENTS

| | | |
|---|---|---|
| JP | 2000-121633 A | 4/2000 |
| JP | 3496154 B2 | 2/2004 |
| JP | 2007-502974 A | 2/2007 |
| KR | 10-2009-0049414 A | 5/2009 |
| WO | 2011-129649 A2 | 10/2011 |

OTHER PUBLICATIONS

Notification of Reasons for Rejection dated Aug. 26, 2016 of corresponding Korean Patent Application No. 10-2013-0083176—4 pages.
Notification of Reasons for Rejection dated Aug. 26, 2016 of corresponding Korean Patent Application No. 10-2013-0083175—4 pages.
Notification of Reasons for Refusal dated Jan. 31, 2017 of corresponding Japanese Patent Application No. 2016-527918—2 pages.

\* cited by examiner

SLIDE ASSEMBLY

TECHNICAL FIELD

The present invention relates to a slide assembly and, more particularly, to a slide assembly for a cytospin.

BACKGROUND ART

As well-known in the art, a cytospin refers to a device by which cells contained in a liquid specimen are concentrated on a limited area of a slide using a centrifugal force. The cells concentrated by the cytospin are directly collected and smeared in a specified position on a slide. In this way, cells to be inspected are collected at one location by the cytospin. By dyeing and observing the cells thus collected, it is possible to clearly see the shape and nature of the cells to be inspected. In particular, the cytospin is effective when a small number of cells are contained in a small amount of liquid specimen. The cytospin is medical equipment which is widely used in the field of cell biology, histology and pathology.

A conventional slide assembly used in the cytospin is illustrated in FIGS. 1A and 1B. As illustrated, the conventional slide assembly 1 includes a slide 2 positioned at a lower side and a filter card 3 disposed on the upper surface of the slide 2. The filter card 3 is an absorption paper that absorbs a liquid. The filter card 3 has a hole 3a formed through the thickness thereof. The hole 3a cooperates with the slide 2 to form an accommodation space 3b. By the operation of a cytospin, a liquid sprayed toward the slide 2 enters the accommodation space 3b. Cells contained in the liquid adhere to the slide 2. The liquid is absorbed to the filter card 3 as indicated by arrows in FIG. 1B.

However, in the conventional slide assembly described above, some of the cells existing in the accommodation space 3b are absorbed to the filter card 3 together with the liquid. Thus, a loss of cells is generated. Particularly, if the number of cells contained in a specimen is important, the loss of cells may lead to a severe error in determining an inspection result. Due to the loss of cells to be inspected, detection target cells may be excluded and a substantial amount of analysis targets may be missing. This may adversely affect quantitative and qualitative inspection results.

SUMMARY OF THE INVENTION

Technical Problems

In view of the aforementioned problems inherent in the prior art, it is an aspect of the present invention to provide a slide assembly capable of preventing a loss of cells to be inspected.

Another aspect of the present invention is to provide a slide assembly capable of enabling accurate qualitative and quantitative analysis of inspection targets by preventing a loss of cells to be inspected.

Technical Solutions

According to one aspect of the present invention for achieving the above, there is provided a slide assembly, including: a slide having a hole formed in a predetermined position and including a mesh filter installed on a lower surface of the slide in alignment with the hole, the mesh filter having a plurality of filtering holes; and a filter card disposed below the slide so as to make contact with the lower surface of the slide.

According to another aspect of the present invention, there is provided a slide assembly, including: a slide including a mounting seat opened at a top end thereof and provided with a discharge hole formed in a wall surface thereof, the mounting seat protruding from an upper surface of the slide; a filter card disposed above the slide, the filter card having an insertion hole into which the mounting seat is inserted; and a collecting member opened at a top end thereof and fitted to the mounting seat, the collecting member including a mesh filter installed under the collecting member.

Preferably, the mesh filter has a surface coated so as to easily collect cells.

Advantageous Effects

The slide assembly according to the present invention has an effect of preventing a loss of cells to be inspected.

The slide assembly according to the present invention has an effect of enabling accurate qualitative and quantitative analysis of inspection targets.

EMBODIMENTS

The above and other objects and features of the present invention will become apparent from the following description of embodiments given in conjunction with the accompanying drawings.

Embodiments of a slide assembly according to the present invention will now be described in detail with reference to the accompanying drawings.

Figure 1A:
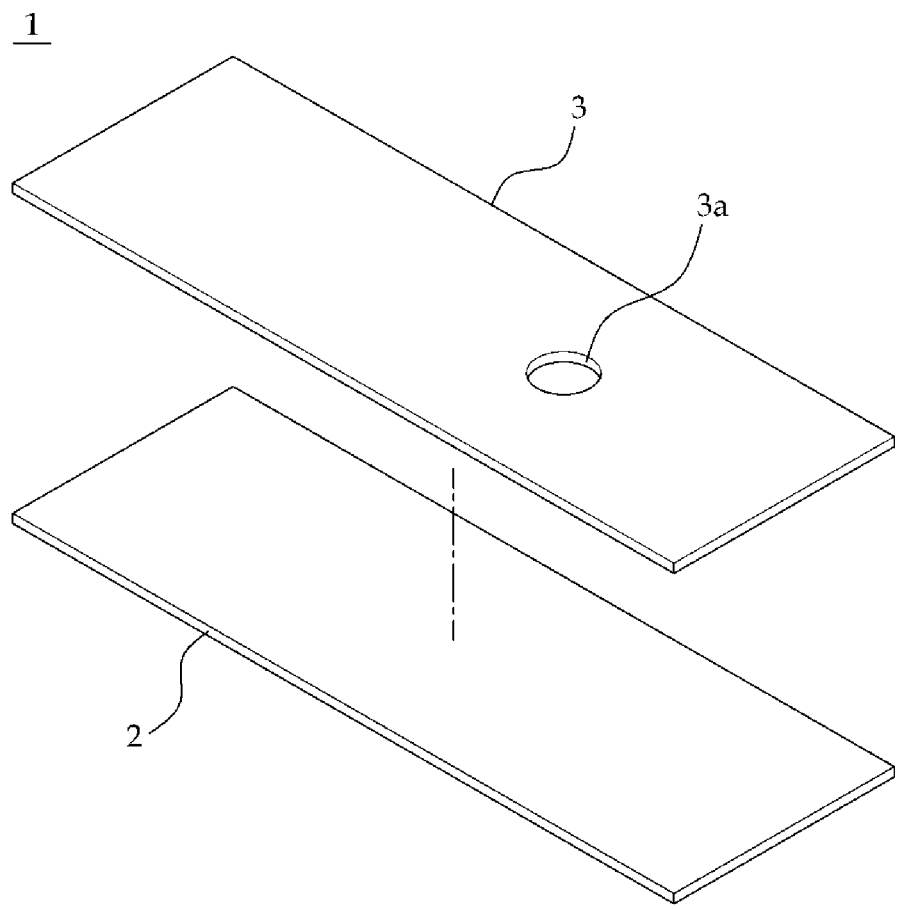
FIG. 1A is an exploded perspective view showing a conventional slide assembly.
Figure 1B:
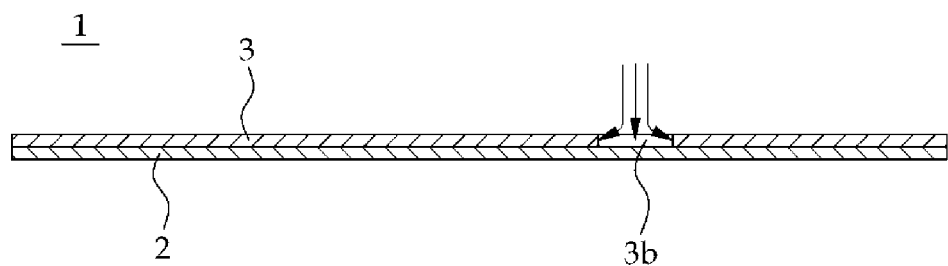
FIG. 1B is a sectional view of the conventional slide assembly.
Figure 2:
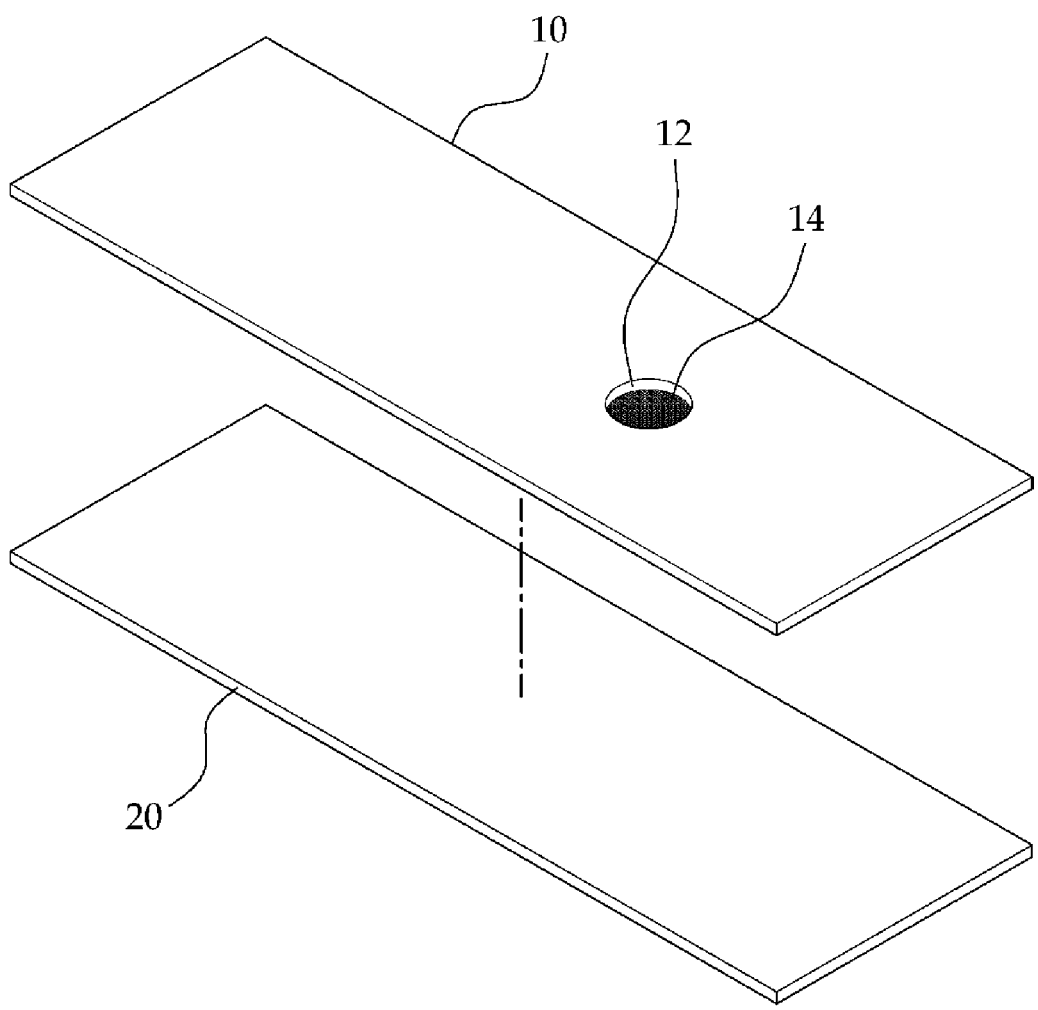
FIG. 2 is an exploded perspective view illustrating a slide assembly according to a first embodiment of the present invention.

Referring to FIG. 2, the slide assembly according to a first embodiment of the present invention includes a slide 10 positioned at an upper side and a filter card 20 as an absorption paper disposed below the slide 10 so as to make contact with a lower surface of the slide 10.

Figure 3:
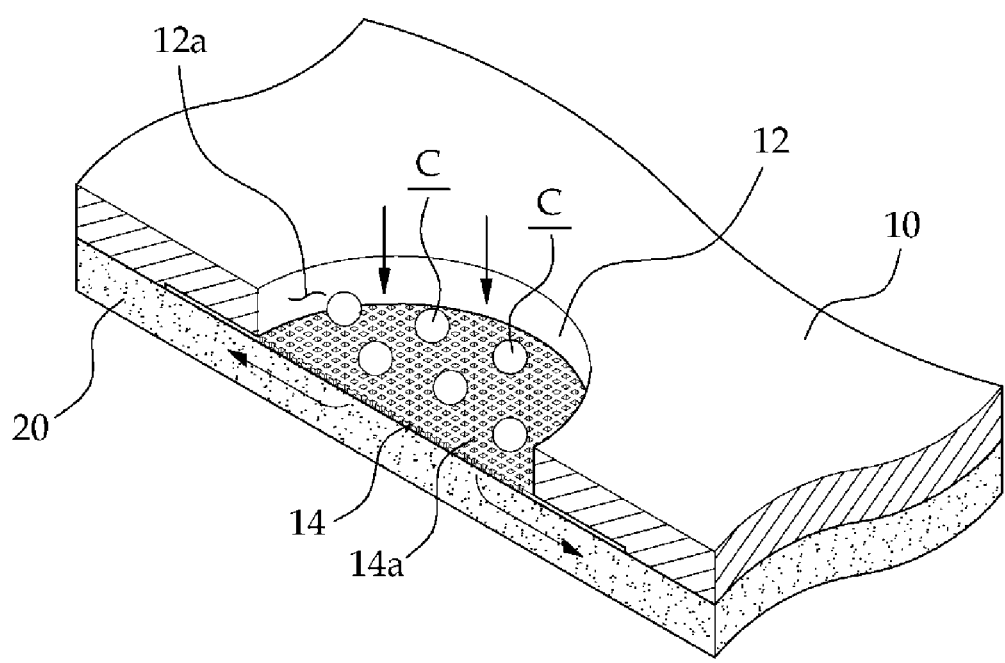
FIG. 3 is a partially cutaway enlarged sectional perspective view of the slide assembly according to the first embodiment of the present invention.

As illustrated in FIGS. 2 and 3, the slide 10 has a hole 12 configured to accommodate a centrifugally-sprayed liquid. A mesh filter 14 is fixedly secured to a lower surface of the slide 10 in alignment with the hole 12. The mesh filter 14 has a plurality of filtering holes 14a having a size capable of filtering cells to be inspected. An accommodation space 12a for collecting cells C is defined by the hole 12 of the slide 10 and the mesh filter 14.

Preferably, the surface of the mesh filter 14 is coated so as to easily collect cells.

Figure 4:
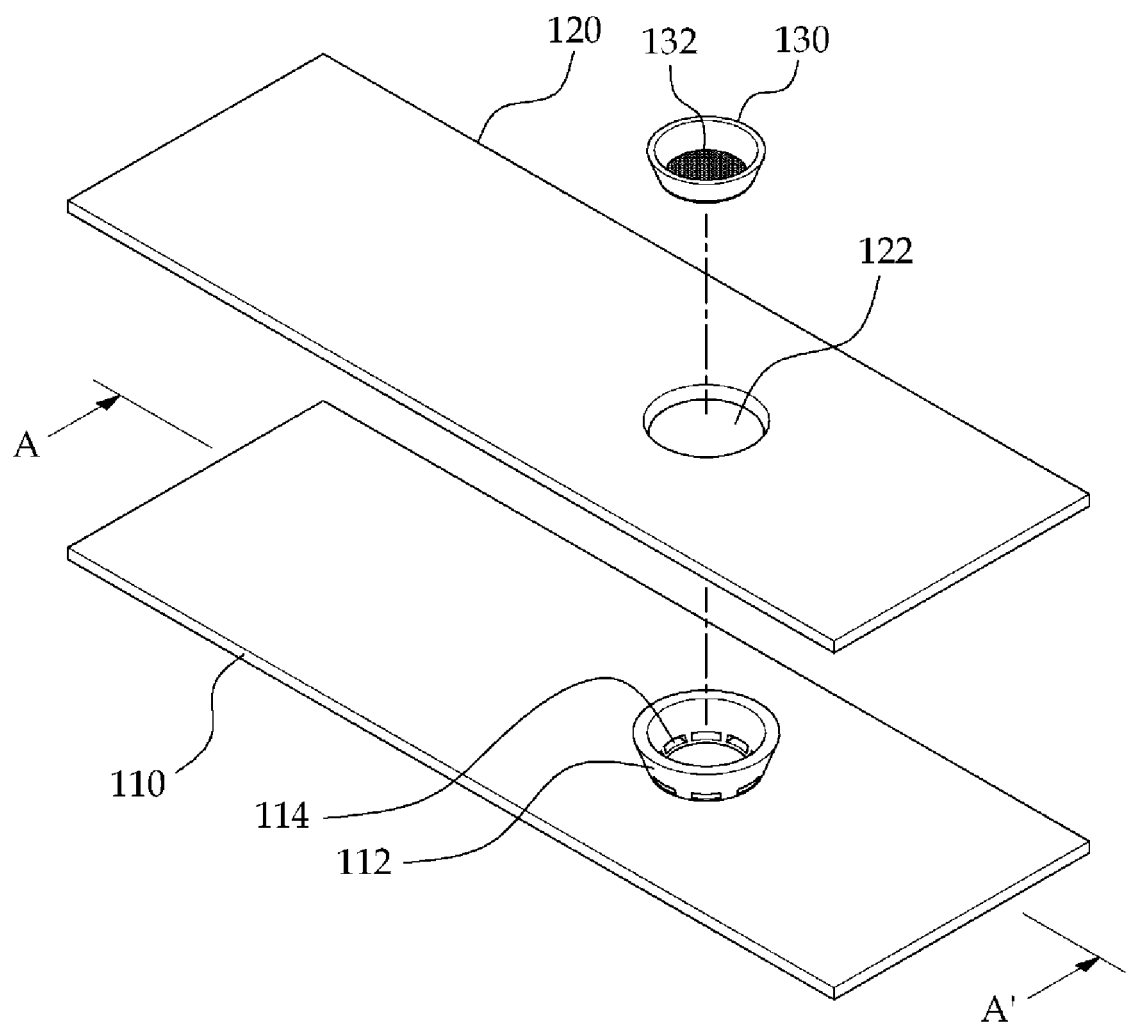
FIG. 4 is an exploded perspective view illustrating a slide assembly according to a second embodiment of the present invention.

Referring next to FIG. 4, a slide assembly according to a second embodiment of the present invention includes a slide 110 positioned at a lower side, a filter card 120 as an absorption paper disposed above the slide 110 so as to make contact with an upper surface of the slide 110, and a collecting member 130 positioned to protrude upward from the filter card 120.

Figure 5:
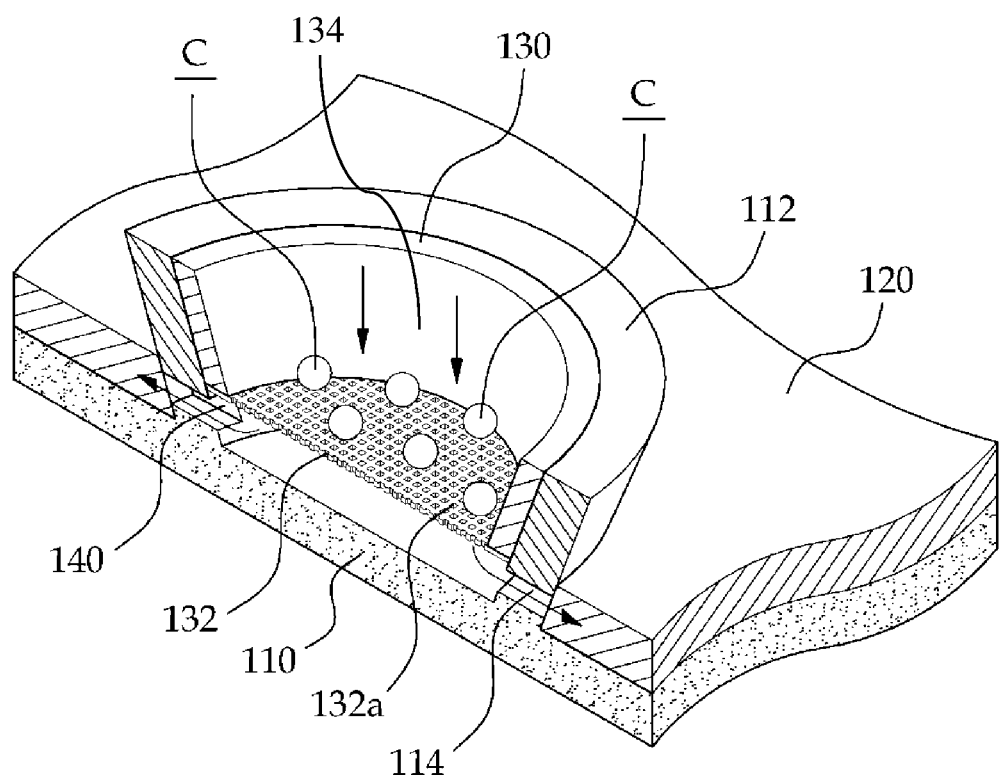
FIG. 5 is a partially cutaway enlarged sectional perspective view of the slide assembly according to the second embodiment of the present invention, which is taken along line A-A' in FIG. 5.

As illustrated in FIGS. 4 and 5, the slide 110 includes a mounting seat 112 protruding from an upper surface of the slide 110. The mounting seat 112 is opened at the top end thereof. The mounting seat 112 has a tapering cross-sectional shape and a diameter growing larger upward so as to smoothly guide a liquid. Discharge holes 14 are formed in a lower wall surface of the mounting seat 112 at specified intervals. While a plurality of discharge holes 114 is formed in the present embodiment, it may be possible to form a single elongated discharge hole.

The filter card 120 is placed on an upper surface of the slide 110. The filter card 120 has an insertion hole 122 aligned with the mounting seat 112 so that the mounting seat 112 is inserted into the insertion hole 122. When the mounting seat 112 is inserted into the insertion hole 122, the mounting seat 112 protrudes upward from the filter card 120.

The collecting member 130 is fitted and fixed to the mounting seat 112. The collecting member 130 is opened at the top end thereof. Similar to the mounting seat 112, the collecting member 130 has a tapering cross-sectional shape and a diameter growing larger upward. The collecting member 130 is fitted to the mounting seat 112 so as to protrude upward beyond the filter card 120. A mesh filter 132 is fixedly secured to a lower portion of the collecting member 130. The mesh filter 132 has a plurality of filtering holes 132a having a size capable of filtering cells to be inspected. An accommodation space 134 for collecting cells C is defined by the collecting member 130 and the mesh filter 132.

Similar to the mesh filter 14 of the first embodiment, the surface of the mesh filter 132 is coated so as to easily collect cells.

Descriptions will now be made on the operations of the slide assemblies according to the embodiments of the present invention, which have the configurations described above.

The operation of the slide assembly according to the first embodiment will be described with reference to FIG. 3. First, a cytospin is operated so that a liquid to be inspected is sprayed toward the slide 10 by a centrifugal force. As indicated by arrows in FIG. 3, the sprayed liquid containing cells enters the hole 12 of the slide 10 and then moves downward. The liquid is moved through the filtering holes 14a and is absorbed to the filter card 20. The cells C to be inspected fail to pass through the filtering holes 14a. Thus, the cells C to be inspected are filtered and collected within the accommodation space 12a.

In the slide assembly according to the first embodiment of the present invention, the cells C are collected in the accommodation space 12a of the slide 10 with no loss. The cells C thus collected are sent to a predetermined next inspection step.

Next, the operation of the slide assembly according to the second embodiment will be described with reference to FIG. 5. As in the first embodiment, a cytospin is operated so that a liquid to be inspected is sprayed toward the slide 110 by a centrifugal force. As indicated by arrows in FIG. 5, the sprayed liquid containing cells enters the accommodation space 134 defined inside the collecting member 130 and then moves downward. The liquid passes through the filtering holes 132a and flows toward the lower side of the mounting seat 112. Subsequently, the liquid is moved outward through the discharge holes 114 and is absorbed to the filter card 120. The cells C to be inspected fail to pass through the filtering holes 132a. Thus, the cells C to be inspected are filtered and collected within the accommodation space 134.

In the slide assembly according to the second embodiment of the present invention, the cells C are collected in the accommodation space 134 of the collecting member 130 with no loss. The cells C thus collected are sent to a predetermined next inspection step.

While embodiments of the present invention have been described above, the present invention is not limited to the aforementioned embodiments. It goes without saying that a person skilled in the relevant art can make various changes and modifications without departing from the scope of the invention defined in the claims. Such changes and modifications shall be construed to fall within the scope of the present invention.

DESCRIPTION OF REFERENCE SYMBOLS 10, 110: slide, 12: hole, 14, 132: mesh filter, 14a: filtering hole, 20, 120: filter card, 112: mounting seat, 114: discharge hole, 130: collecting member, 134: accommodation space, C: cell

What is claimed is:

1. A slide assembly, comprising:
a collecting cup comprising a bottom mesh filter;
a slide including an upper surface;
a mounting seat cup integrated with the slide, the mounting seat cup comprising a sidewall upwardly extending from the upper surface of the slide, a portion of the upper surface providing a bottom of the mounting seat cup, wherein the mounting seat cup is configured to receive the collecting cup such that the mounting seat cup and the collecting cup in combination at least temporarily contain liquid poured into the collecting cup;
a filter card comprising an opening and configured to be placed over the upper surface of the slide such that the mounting seat cup is inserted into the opening; and
a discharge through-hole formed in the mounting seat cup and configured for discharging therethrough liquid contained in the collecting cup and the mounted seat cup.

2. The slide assembly of claim 1, wherein an upper surface of the collecting cup is positioned higher than an upper surface of the filter card when the collecting cup is received in the mounting seat cup and the filter card is placed over the slide.

3. The slide assembly of claim 2, wherein each of the mounting seat cup and the collecting cup have a tapered shape.

4. The slide assembly of claim 3, wherein the discharge through-hole of the mounting seat cup extends in a circumferential direction.

5. The slide assembly of claim 1, wherein the discharge through-hole of the mounting seat cup extends in a circumferential direction.

* * * * *